(12) United States Patent  (10) Patent No.: US 8,672,881 B2
Nagamatsu  (45) Date of Patent: Mar. 18, 2014

(54) SYRINGE SET FOR BALLOON CATHETER

(75) Inventor: Ryuji Nagamatsu, Hachioji (JP)

(73) Assignee: Olympus Corporation (JP)

( * ) Notice: Subject to any disclaimer, the term of this patent is extended or adjusted under 35 U.S.C. 154(b) by 652 days.

(21) Appl. No.: 12/123,603

(22) Filed: May 20, 2008

(65) Prior Publication Data
US 2008/0221515 A1    Sep. 11, 2008

Related U.S. Application Data

(60) Continuation of application No. 11/493,192, filed on Jul. 26, 2006, now abandoned, which is a division of application No. 11/128,092, filed on May 11, 2005, now abandoned.

(51) Int. Cl.
*A61M 29/00* (2006.01)
*B65D 83/10* (2006.01)

(52) U.S. Cl.
USPC ........................ 604/97.02; 206/364

(58) Field of Classification Search
USPC ......... 604/97.02, 154, 80, 191, 241–2, 97.01, 604/97.03; 206/364, 366, 229, 365, 363
See application file for complete search history.

(56) References Cited

U.S. PATENT DOCUMENTS

| | | | | |
|---|---|---|---|---|
| 3,305,084 A | * | 2/1967 | Higgins et al. ................ 206/366 |
| 3,871,374 A | * | 3/1975 | Bolduc et al. ................ 128/831 |
| 4,323,071 A |   | 4/1982 | Simpson et al. |
| 4,795,431 A | * | 1/1989 | Walling ...................... 604/97.02 |
| 4,795,441 A | * | 1/1989 | Bhatt ........................... 604/124 |
| 5,007,535 A | * | 4/1991 | Meseke et al. ............... 206/366 |
| 5,289,919 A | * | 3/1994 | Fischer ........................ 206/571 |
| 5,376,079 A | * | 12/1994 | Holm ........................... 604/191 |
| 5,529,463 A | * | 6/1996 | Layer et al. .................. 417/403 |
| 5,643,206 A | * | 7/1997 | Fischer ......................... 604/82 |
| 5,955,020 A | * | 9/1999 | Gholson ....................... 264/262 |
| 6,228,324 B1 |   | 5/2001 | Hasegawa et al. |

(Continued)

FOREIGN PATENT DOCUMENTS

| | | |
|---|---|---|
| JP | 6-503271 | 4/1994 |
| JP | 11-155948 | 6/1999 |
| WO | WO 93/06940 | 4/1993 |
| WO | WO 02/083021 | 10/2002 |

OTHER PUBLICATIONS

Office Action issued by the Japanese Patent Office on Aug. 24, 2009 in connection with corresponding Japanese Patent Application No. 2004-143616 and English translation thereof.

(Continued)

*Primary Examiner* — Kevin C Sirmons
*Assistant Examiner* — Andrew Gilbert
(74) *Attorney, Agent, or Firm* — Ostrolenk Faber LLP

(57) ABSTRACT

A syringe holder which is capable of holding a plurality of types of syringes used for expanding a balloon catheter so as to be capable of being detached and attached is proposed. Preferably, a clearance is provided between the syringe holder and the syringe, so that gas can come into sufficient contact therewith during sterilizing treatment. The syringe holder in this arrangement can be formed, for example, by forming a plurality of grooves which are similar to the shape of the syringe and slightly larger than the syringe on a sheet formed of resilient member. Preferably, the shape is devised to prevent dropping off of the syringe from the syringe holder.

15 Claims, 9 Drawing Sheets

(56) References Cited

U.S. PATENT DOCUMENTS

| | | | |
|---|---|---|---|
| 6,371,975 B2 * | 4/2002 | Cruise et al. | 606/214 |
| 6,471,671 B1 * | 10/2002 | Urick et al. | 604/98.01 |
| 6,796,875 B1 * | 9/2004 | Placik | 450/1 |
| 7,308,985 B2 * | 12/2007 | Riley | 206/570 |
| 2002/0185406 A1 * | 12/2002 | Massengale et al. | 206/571 |
| 2003/0018301 A1 | 1/2003 | Sheppard et al. | |
| 2003/0199816 A1 * | 10/2003 | Ramming | 604/89 |
| 2004/0055826 A1 * | 3/2004 | Bowers | 184/105.1 |

OTHER PUBLICATIONS

Search Report issued by European Patent Office on Jun. 19, 2007 in connection with corresponding EP application 07 00 9259.

* cited by examiner

SYRINGE SET FOR BALLOON CATHETER

CROSS-REFERENCE TO RELATED APPLICATIONS

The present application is a continuation of prior application Ser. No. 11/493,192, filed Jul. 26, 2006, by Ryuji NAGAMATSU, entitled SYRINGE HOLDER FOR BALLOON CATHETER AND SYRINGE SET FOR BALLOON CATHETER, now abandoned, which is a divisional of U.S. application Ser. No. 11/128,092 filed May 11, 2005, by Ryuji NAGAMATSU, entitled SYRINGE HOLDER FOR BALLOON CATHETER AND SYRINGE SET FOR BALLOON CATHETER, now abandoned, which claims the benefit of priority from prior Japanese Patent Application No. 2004-143616, filed on May 13, 2004, the entire contents of which is incorporated herein by reference.

BACKGROUND OF THE INVENTION

1. Field of the Invention

The present invention relates to a technique to store and retain a syringe used for a balloon catheter. More specifically, the invention relates to a syringe holder and a syringe set with the syringe stored in the syringe holder.

2. Description of the Related Art

A balloon catheter is an instrument for administering medical treatment for a living body. The balloon catheter includes a catheter to be inserted into a body, and is provided with a balloon at the distal end of the catheter. The balloon is formed by covering a tube on the outer periphery of the catheter and fixing the both ends thereof. The catheter is formed with a lumen communicating with the inside of the balloon, and the balloon can be inflated by sending air into the lumen (for example, see JP-A-2002-143311).

In the related art, when using the balloon catheter in a luminal structure, barium meal is used for taking X-ray movie for control the amount of air to be supplied while observing the diameter of the balloon in many cases. In this case, the balloon can be observed clearly along the outline thereof at a portion pushed against an inner wall of the luminal structure since the barium meal is moved away at this portion. However, at a portion of the balloon which is hidden by the barium meal, the outline thereof cannot be observed clearly, and hence the precise size of the balloon cannot be obtained.

To cope with this problem, there is a technique for providing a plurality of syringes having different capacities in advance so that the size of the balloon can be controlled without using X-rays, and using a syringe of a desired capacity in connection with the balloon catheter for controlling the size of the balloon. In this case, the plurality of syringes are prepared in a sterilized packages for the balloon catheter and a required syringe is taken out from the sterilized package for use. Alternatively, there is a case where a plurality of syringes are stored in a sterilized package and the sterilized package is stored in another sterilized package for the balloon catheter.

However, in the case where the plurality of syringes are stored in the sterilized package, the syringes are often scattered in the sterilized package during transportation, and hence it is difficult to take a required syringe. When the sterilized package in which only the syringes are stored is stored in another sterilized package, since the syringes are packed twice, it takes time for taking the syringe out. In view of efficiency of manipulation, it is preferable that an operator can select a syringe optimal for manipulation easily out of the plurality of syringes that are similar in appearance.

BRIEF SUMMARY OF THE INVENTION

The present invention provides a syringe holder for a balloon catheter which can hold a plurality of syringes so as to be capable of being attached and detached.

In this arrangement, the plurality of syringes can be treated together as a single unit. Since the syringes are held so as to be capable of being attached and detached, an operator can take only a required syringe when in use.

Preferably, a holding part for holding the syringe is formed with an allowance with respect to the contour of the syringe, and an inner surface includes at least one protrusion.

In this arrangement, the syringe and the syringe holder do not come into tight-contact with each other and there exists a clearance therebetween. Since the syringe is supported by the protrusion, the contact area between the syringe and the holding part is reduced. It has an advantage in that gas can intrude easily into the syringe during sterilizing treatment. As a method of defining the clearance, a non-circular cross-section may be employed for the holding part.

Preferably, the sizes of the plurality of holding parts are not identical, so as to be capable of accommodating the syringes having different outer diameters.

In this arrangement, the plurality of syringes having different sizes can be accommodated. This is an advantageous characteristic for a case in which the amount of expansion of the balloon is controlled by the size of the syringe which supplies fluid. Since the operator can select a suitable syringe out of the plurality of syringes having different sizes by intuition, the working efficiency is improved.

Preferably, the holding part includes a flat portion for constraining rotation of the syringe by coming into abutment with a flange of the syringe.

In this arrangement, the rotation of the syringe stored in the syringe holder can be constrained. Therefore, when there are indications on the surfaces of the syringes, a uniform orientation of the indications is achieved, and hence visibility is improved.

Preferably, the holding part is formed with an opening for allowing a distal portion of the syringe on the side of a connecting portion thereof to be projected, which is to be connected to the balloon catheter.

In this arrangement, the syringe can be separated from the syringe holder easily by gripping the projected portion.

The holding part may be, for example, a storage groove, which is a groove having an opening to which the syringe can be inserted. When the holding part is the groove, the syringe can be inserted easily from the opening. When the storage groove is employed, a projection for preventing the stored syringe from coming off may be provided at an upper portion thereof. When the syringe holder has resiliency, the syringe can be inserted easily by widening the opening by resilient deformation.

By adapting the shape of the storage groove to the shape of the syringe, the operator can know the storing position or the storing direction of the syringe with a glance. More specifically, the storage groove includes at least a cylinder storage groove for storing the cylinder of the syringe, a flange storage groove for storing the flange of the syringe, and a plunger storage groove for storing a plunger of the syringe so as to communicate with each other.

It is preferable to provide a device for preventing the syringe or the plunger of the syringe from dropping off. For example, the size of the cylinder storage groove is determined to be smaller than that of the flange of the syringe, so that the cylinder of the syringe is prevented from moving and dropping off in the axial direction. The plunger storage groove is closed at one end surface so that the plunger of the syringe is prevented from coming off and dropping off from the cylinder.

Preferably, the storage groove prevents the axial rotation of the syringe. It is because the syringe is stabilized, and the position of indication formed on the syringe is also kept constant.

The invention may also be understood as a syringe set combining the syringe holder and the syringe stored in the syringe holder.

According to the invention, the plurality of syringes can be stored in the syringe holder. Therefore, when the syringe holder is stored in the sterilized package, the syringes are prevented from being scattered in the sterilized package, and hence can be treated as a single unit. Therefore, handling in use or selection of a syringe is facilitated. Therefore, the manipulation can be facilitated, and the manipulation time can be reduced.

When the allowance is provided in the storage groove of the syringe holder, since a clearance is defined between the syringe holder and the syringe, sterilization by gas such as ethylene oxide gas can easily be achieved. In addition, by reducing the contact area between the syringe and the syringe holder by the protrusion, the clearance between the syringe and the syringe holder can be sterilized further reliably.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE DRAWINGS

Preferred embodiments of the invention will be described below with reference to the accompanying drawings.

Figure 1:
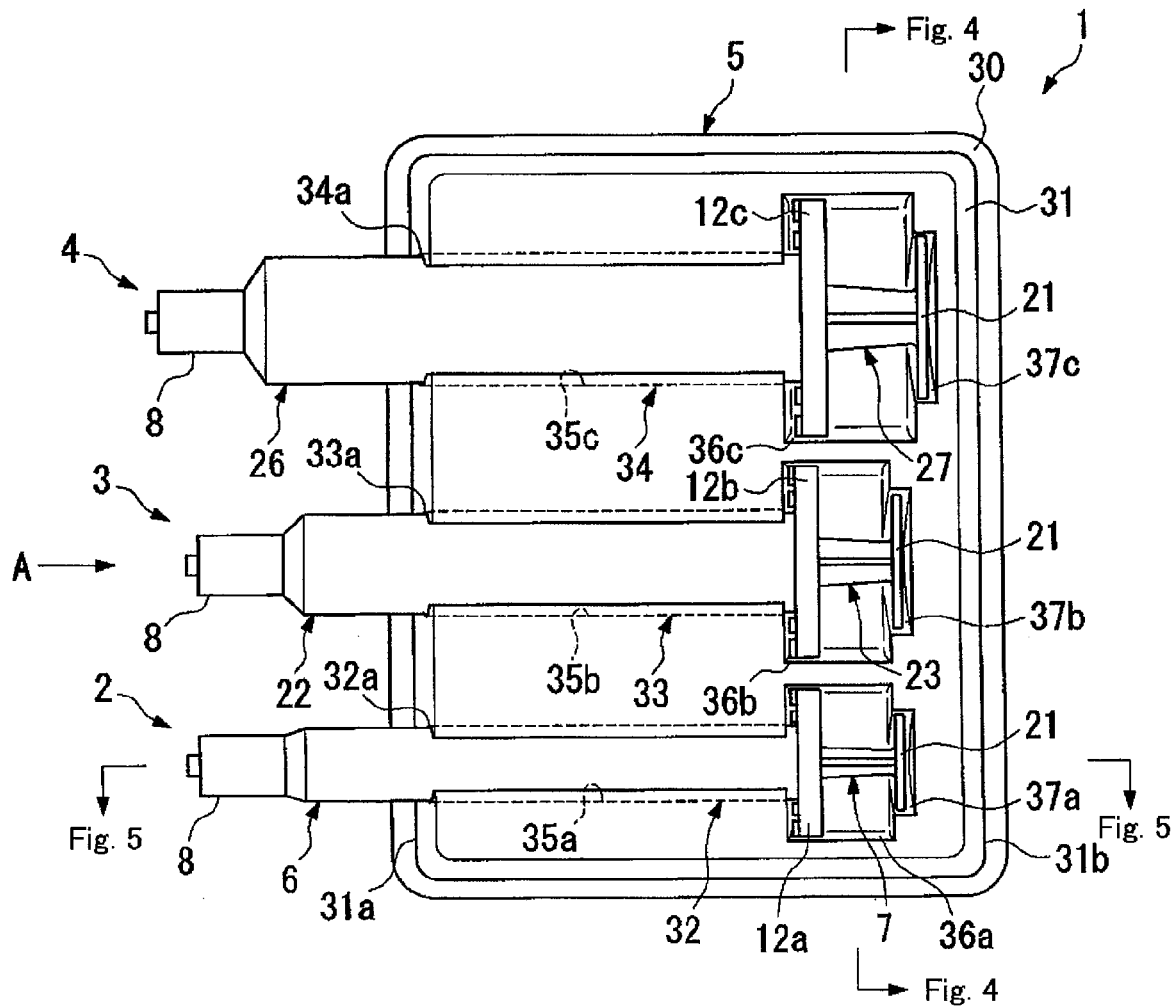
FIG. 1 is a top view of a syringe set according to an embodiment of the invention.
Figure 2:
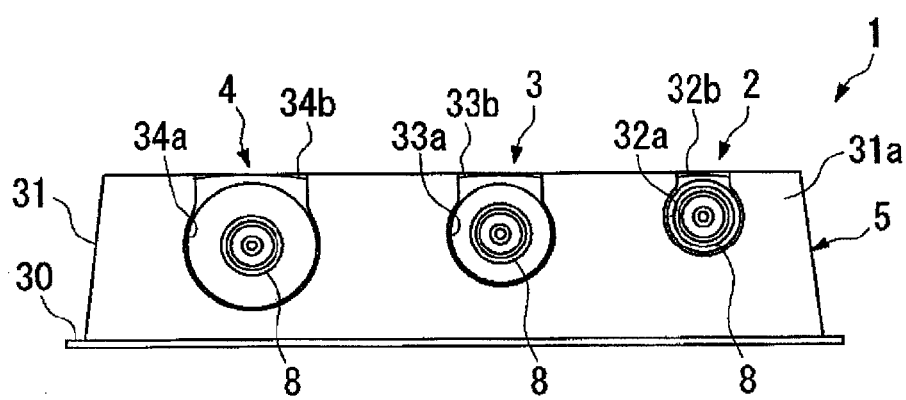
FIG. 2 is a drawing viewed in the direction indicated by an arrow A in FIG. 1.

FIG. 1 and FIG. 2 show a syringe set 1 having three syringes 2, 3 and 4 with different capacities stored in a syringe holder 5.

Figure 3A:
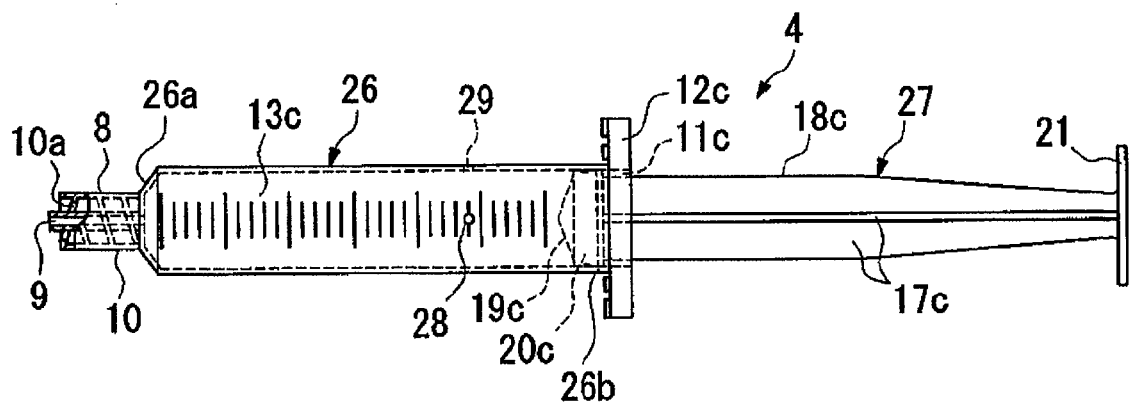
FIG. 3 is a drawing showing a structure of a syringe.
Figure 3B:
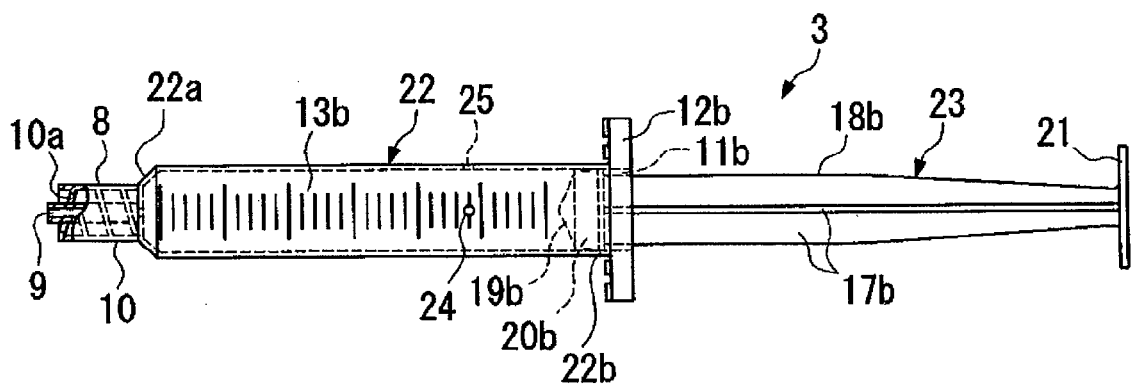
Figure 3C:
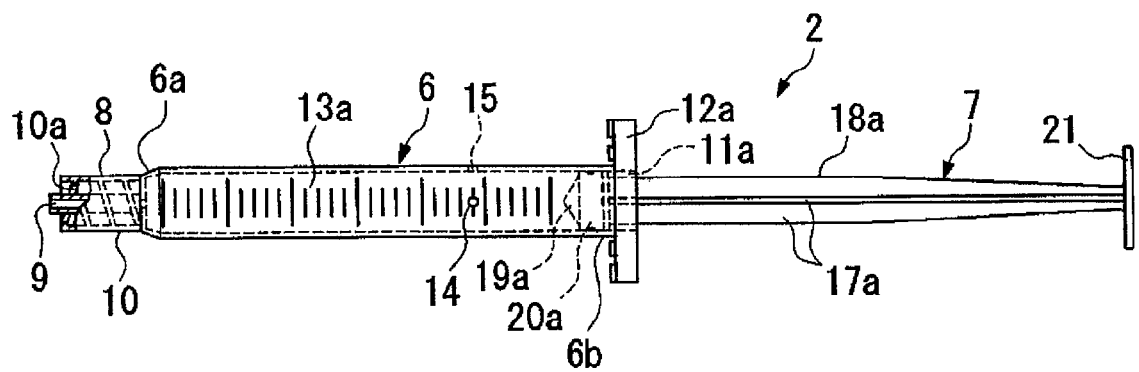

The syringes 2, 3 and 4 are shown in FIG. 3A to FIG. 3C. As shown in FIG. 3C, the syringe 2 includes a cylinder 6 as an outer cylindrical member and a plunger (push rod) 7 to be slidably inserted into the cylinder 6.

The cylinder 6 includes a distal portion 6a having smaller diameter at the distal end thereof, and a connecting portion 8 extends therefrom along the axial line. The connecting portion 8 is formed with an outlet port 9 for communicating the interior of the cylinder 6 with the outside along the axial line thereof. The outlet port 9 is for introducing air to a balloon catheter, described later. The connecting portion 8 is also provided with a cylindrical portion 10 so as to cover the outlet port 9, and the cylindrical portion 10 is formed with an inner thread 10a. A proximal portion 6b of the cylinder 6 is formed with an insertion port 11a so as to allow the plunger 7 to be inserted therein. The proximal portion 6b of the cylinder 6 is formed also with a flange 12a extended in the direction substantially orthogonal to the axial line of the cylinder 6 and in the radial direction of the cylinder 6. The cylinder 6 has a substantially uniform inner diameter to the insertion port 11a at the proximal portion 6b except for the distal portion 6a with reduced diameter. The inner peripheral surface near the insertion port 11a is formed with a projection (not shown) for preventing the plunger 7 from coming off.

The cylinder 6 is formed with a scale 13a on the outer peripheral surface along the axial line thereof. The scale 13a shows a capacity of a space formed in the cylinder with reference to the side of the distal portion 6a. However, the scale is not limited thereto, and may be that indicating the outer diameter of the expended balloon when a seal member 19a, described later, is moved from the position on the scale to the distal end.

The cylinder 6 is formed with a hole 14 so as to align with the scale 13a. The hole 14 communicates between the inside and the outside of the cylinder 6, and is formed at a position where a predetermined capacity (first capacity) is defined in the cylinder 6. The first capacity corresponds, for example, to the amount of air which expands the balloon to 8.5 mm in diameter.

The cylinder 6 is also formed with a hole 15 at a position shifted from the hole 14 by about ¼ turn in the circumferential direction (about 90° in angle). The hole 15 communicates between the inside and the outside of the cylinder 6, and has substantially the same size as the hole 14.

The plunger 7 has a main body 18a formed by two plate strips 17a intersected into a cross-shape. The main body 18a has a size which can be inserted into the cylinder 6, and is attached with the seal member 19a at the distal end thereof. The seal member 19a has a sealing surface 20a which is kept in sliding contact with the inner peripheral surface of the cylinder 6, so as to establish air-tightness between the inner peripheral surface of the cylinder 6 and the seal member 19a. The main body 18a is provided with a disk-shaped pressing portion 21 at the proximal end thereof.

As shown in FIG. 3B, the syringe 3 includes a cylinder 22 which is larger in inner diameter and in outer diameter than the syringe 2, and a plunger 23 to be slidably inserted into the cylinder 22, and has the same structure as the syringe 2. In other words, the cylinder 22 is provided with the connecting portion 8 at a distal portion 22a, and is formed with an insertion port 11b at a proximal portion 22b. The proximal portion 22b is provided with a flange 12b extended therefrom. The cylinder 22 is formed with two holes 24, 25 at a position corresponding, for example, to the amount of air (second capacity) which expands the balloon to 11.5 mm in diameter with reference to the distal portion 22a. The hole 24 is formed on a scale 13b, and the hole 25 is formed at a position shifted by about 90° in the circumferential direction from the hole 24. The plunger 23 has a size corresponding to the cylinder 22, and a main body 18b having plate strips 17b intersected to each other is provided with a seal member 19b at the distal end thereof. The seal member 19b is formed with a sealing surface 20b on the outer peripheral surface thereof which is kept in sliding contact with the inner peripheral surface of the cylinder 22 so as to establish air-tightness.

As shown in FIG. 3A, the syringe 4 includes a cylinder 26 larger than the syringe 3 in inner diameter and outer diameter, and a plunger 27 to be slidably inserted in the cylinder 26, and has the same structure as the syringes 2 and 3. In other words, the cylinder 26 is provided with the connecting portion 8 at a distal portion 26a thereof, and an insertion port 11c at the proximal portion 26b. The cylinder 26 is also provided with a flange 12c at a proximal portion 26b thereof. The cylinder 26 is formed with two holes 28, 29 at positions corresponding, for example, to the amount of air (third capacity) which can expand the balloon to 15 mm in diameter with reference to the distal portion 26a. The hole 28 is provided on a scale 13c, and the hole 29 is formed at a position shifted by about 90° from the hole 28 in the circumferential direction. The plunger 27 has a size corresponding to the cylinder 26 and a main body 18c having plate strips 17c intersected to each other is provided with a seal member 19c at the distal end thereof. The seal member 19c has a sealing surface 20c on the outer peripheral surface thereof which is kept in sliding contact with the inner peripheral surface of cylinder 26 so as to establish air-tightness therebetween.

The syringe set 1 including the aforementioned syringes 2, 3 and 4 and the syringe holder 5 for storing these syringes is shown in FIG. 1 and FIG. 2. The syringe holder 5 has a main body 31 formed of a sheet of substantially rectangular in plan view having a flange 30 along the peripheral edge thereof, and the inner side of the flange is protruded upward. The main body 31 is formed into a trapezoidal shape in side view, in which the flange 30 corresponds to the bottom side. The shorter side of the main body 31 is shorter than the length of the syringes 2, 3 and 4. The main body 31 includes a side surface 31a and a side surface 31b located on the side opposite from the side surface 31a.

The main body 31 is further formed with three recessed holding parts 32, 33 and 34 arranged along the longer side of the main body 31 in parallel with each other. The holding part 32 is used for storing the syringe 2 having the smallest capacity, the holding part 33 is used for storing the syringe 3, and the holding part 34 is used for storing the syringe 4 having the largest capacity.

As shown in FIG. 1, the holding part 32 includes a storage groove opening on the upper side, and the storage groove is partitioned into a cylinder storage groove 35a, a flange storage groove 36a, and a plunger storage groove 37a from the side of the side surface 31a. These grooves 35a, 36a and 37a communicate with each other, and the main body 31 is formed with an opening 32a on the side surface 31a and the opposing side surface 31b of the main body 31 is closed.

The cylinder storage groove 35a has larger width and depth in comparison with the diameter of the cylinder 6 and, in addition, the edge of an upper opening 32b of the cylinder storage groove 35a is protruded so as to reduce the width of the upper opening 32b.

Figure 4:
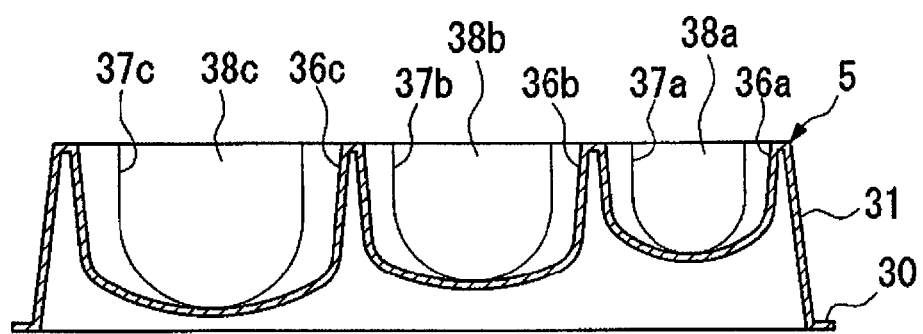
FIG. 4 is a cross-section of FIG. 1 showing a case in which the syringes are not mounted.
Figure 5:
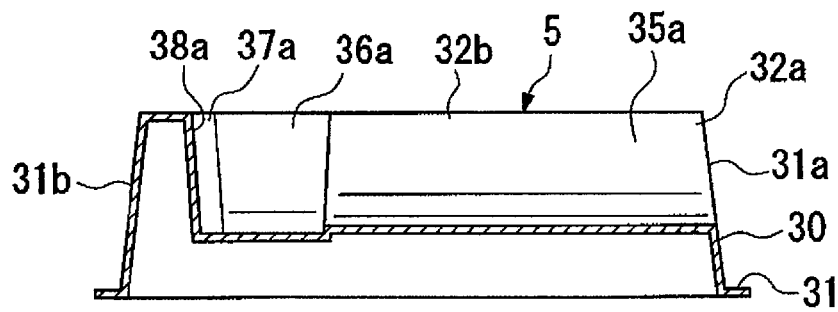
FIG. 5 is a cross-section of FIG. 1 showing a case in which the syringes are not mounted.

The flange storage groove 36a continues to the cylinder storage groove 35a, and is larger than the cylinder storage groove 35a in width. FIG. 4 is a cross-sectional view taken along a cutting line (FIG. 4-FIG. 4) in FIG. 1, showing that no syringe is mounted. As shown in FIG. 4, a side wall of the flange storage groove 36a has an inclination being reduced in width toward the bottom, and the bottom has a form of a smooth depression. FIG. 5 shows a cross-sectional view taken along a cutting line (FIG. 5-FIG. 5) in FIG. 1, showing that no syringe is mounted. As shown in FIG. 5, the depth of the flange storing groove 36a is deeper than that of the cylinder storage groove 35a, and a boundary plane between the flange storage groove 36a and the cylinder storage groove 35a is formed to have an inclination. In the same manner, a boundary plane between the flange storage groove 36a and the plunger storage groove 37a is formed to have an inclination.

The depth of the plunger storage groove 37a is almost the same as that of the flange storage groove 36a, and the radius of curvature of the bottom is smaller than that of the pressing portion 21 of the plunger 7. As shown in FIG. 4, the width of the plunger storage groove 37a is smaller than that of the flange storage groove 36a. The side surface 31b side of the plunger storage groove 37a is closed by a closed surface 38a, and the closed surface 38a is inclined so that the depth of the plunger storage groove 37a is reduced toward the bottom (see FIG. 5).

As shown in FIG. 1 and FIG. 4, the storage groove of the holding part 33 is partitioned into a cylinder storage groove 35b, a flange storage groove 36b, and a plunger storage groove 37b, and an opening 33a is formed on the side surface 31a side. The width and the depth of the cylinder storage groove 35b are larger than those of the cylinder storage groove 35a. The width and the depth of the flange storage groove 36b are larger than those of the cylinder storage groove 35b, and the bottom is formed into a recessed shape. The depth of the plunger storage groove 37b is about the same as that of the flange storage groove 36b, and the width thereof is smaller than that of the flange storage groove 36b. The closed surface 38b on the side of the side surface 31b of the plunger storage groove 37b, a boundary plane between the plunger storage groove 37b and the flange storage groove 36b, and a boundary plane between the flange storage groove 36b and the cylinder storage groove 35b are inclined as in the same manner as the surfaces corresponding to the holding part 32.

The holding part 34 has the same structure as the holding part 33 except that the width and the depth are different. In other words, the holding part 34 is provided with an opening 34a on the side surface 31a side, and is partitioned into a cylinder storage groove 35c, a flange storage groove 36c and a plunger storage groove 37c. The width and the depth of the flange storage groove 36c are larger than those of the cylinder storage groove 35c, and the bottom is formed into a recessed shape. The depth of the plunger storage groove 37c is almost the same as that of the flange storage groove 36c, and the width thereof is smaller than that of the flange storage groove 36c. The closed surface 38c on the side of the side surface 31b of the plunger storage groove 37c, a boundary plane between the plunger storage groove 37c and the flange storage groove 36c, and a boundary plane between the flange storage groove 36c and the cylinder storage groove 35c are inclined as in the same manner as the surfaces corresponding to the holding parts 32, 33.

The syringe holder 5 as described above is formed by vacuum-molding a sheet material having flexibility, such as polypropylene or polyethylene, polystyrene or polyethylene terephthalate, polycarbonate or ABS (acetonitrile butadiene styrene), metacrylate resin.

Figure 6:
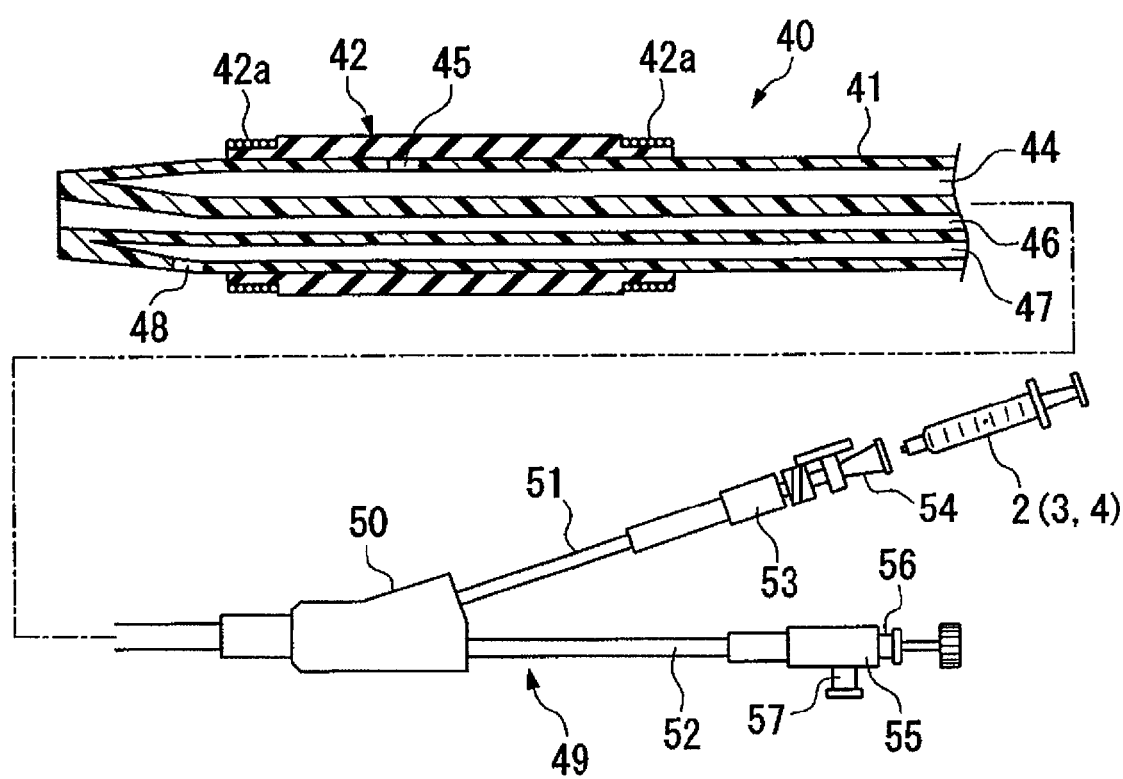
FIG. 6 is a cross-sectional view showing an example of a balloon catheter.
Figure 7:
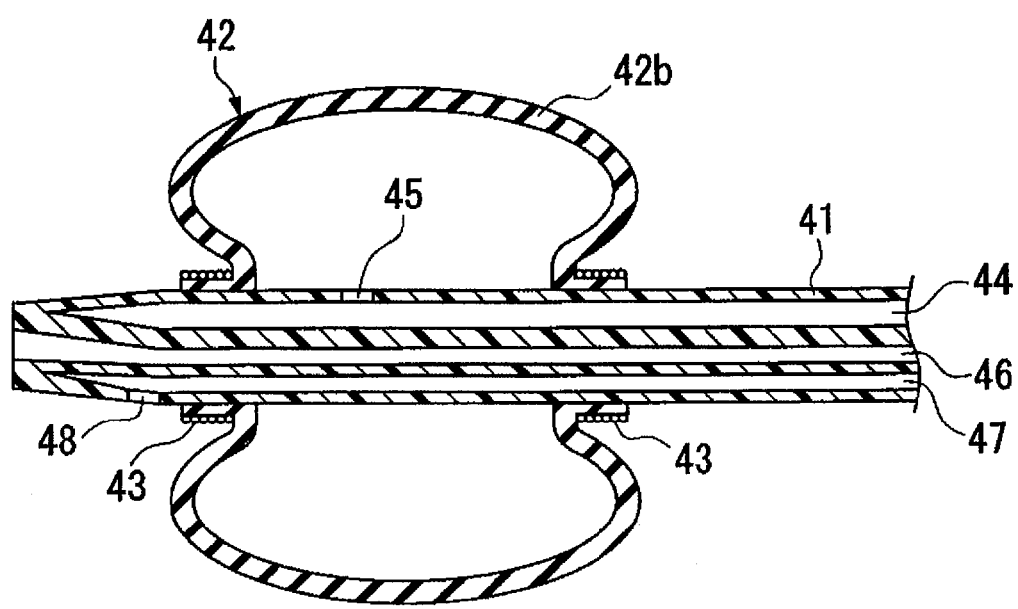
FIG. 7 is a cross-sectional view showing the distal portion of the balloon catheter.

Referring now to FIG. 6 and FIG. 7, an example of a balloon catheter to be stored in the sterilized package together with the syringe set 1 will be described.

FIG. 6 shows a balloon catheter 40 and an operating portion 49. The balloon catheter 40 includes a flexible catheter (sheath) 41 to be inserted into the luminal structure, and a balloon 42 is mounted to the distal end of the catheter 41. The balloon 42 is a tube formed, for example, of natural rubber latex, and the distal portion of the catheter 41 is inserted through the tube, and then both ends 42a thereof are fixed by being bound by strings 43 (FIG. 7) and applied with adhesive agent. When air is supplied to the balloon 42, an intermediate portion 42b which is not fixed can be expanded, as shown in FIG. 7.

An expansion lumen 44 is formed in the catheter 41. The expansion lumen 44 is closed at the distal portion thereof, and is formed with a side hole 45 in communication with the intermediate portion 42b of the balloon 42. The catheter 41 is formed therein with a guide lumen 46 and a liquid-delivery lumen 47 arranged in substantially parallel to each other. A guide wire or a stylet is inserted through the guide lumen 46 when inserting the distal portion of the catheter 41 into the luminal structure. The liquid-delivery lumen 47 is used for injecting the barium meal into the luminal structure. The distal portion of the liquid-delivery lumen 47 is closed and is provided with a side hole 48 for communicating with the outside. It is also possible to inject the barium meal using the guide lumen 46 instead of forming the liquid-delivery lumen 47.

The catheter 41 is provided with the operating portion 49 at the proximal portion thereof. The operating portion 49 includes a blanch member 50 connected to the catheter 41, an expansion shaft 51 and a guide shaft 52 are extended from the branch member 50. The expansion shaft 51 is formed therein with a lumen which communicates with the expansion lumen 44, and the expansion shaft 51 is provided with a pipe sleeve 53 of a lure-shape at the proximal portion thereof. One of the syringes 2, 3 and 4 is connected to the pipe sleeve 53 via a valve 54. A pipe sleeve 55 is mounted to the proximal portion of the guide shaft 52. The pipe sleeve 55 is provided with two inlets 56, 57. The inlet 56 is in communication with the guide lumen 46, and a guide wire is inserted therethrough to enhance rigidity of the catheter 41 and hence the pushability can be improved. The inlet 57 is communicated with the liquid-delivery lumen 47, so that a syringe for barium meal in which barium meal is stored can be connected thereto.

Subsequently, the operation of the syringe set 1 and the syringe holder 5 will be described.

The syringe 2 is stored in the holding part 32 of the syringe holder 5. More specifically, the syringe 2 is pushed in the syringe holder 5 from the upper opening 32b so that the flange 12a of the cylinder 6 is stored in the flange storage groove 36a. The cylinder 6 is inserted so as to open the edge of the upper opening 32b of the cylinder storage groove 35a. At this time, since the length of the cylinder storage groove 35a is shorter than the cylinder 6, the distal portion 6a side of the cylinder 6 projects from the side surface 31a of the syringe holder 5. The flange 12a of the cylinder 6 is stored in the flange storage groove 36a, and the pressing portion 21 is stored in the plunger storage groove 37a.

The width and the depth of the cylinder storage groove 35a are larger than those of the cylinder 6 of the syringe 2, so that an allowance is formed with respect to the syringe 2. Therefore, high-pressure steam in the autoclave for sterilizing treatment or ethylene oxide gas can easily permeate therein. Since the flange 12a of the syringe 2 and the boundary plane between the flange storage groove 36a and the cylinder storage groove 35a come into abutment with each other, the syringe 2 is prevented from dropping off from the side of the opening 32a. Since the plunger storage groove 37a side is closed by the closed surface 38a, the syringe 2 does not come off from this side.

In the same manner, the syringe 3 is inserted from the upper opening 33b into the holding part 33 so as to be held thereby, and the syringe 4 is inserted from the upper opening 34b into the holding part 34 so as to be held thereby.

The syringe set 1 having the respective syringes 2, 3 and 4 stored in the syringe holder 5 is stored in a sterilized package (not shown). After having stored additional members such as the balloon catheter 40 shown in FIG. 6, the sterilized package is sealed, and subjected to sterilizing treatment. The sterilizing treatment includes high-pressure steam sterilization by the autoclave, or sterilization by ethylene oxide gas.

When inserting the balloon catheter 40 into the luminal structure and expanding the balloon 42, the inner thread 10a of the connecting portion 8 of a selected one of the three syringes 2, 3 and 4 is screwed onto the valve 54 to connect the same. When removing the syringe 2, 3 or 4 from the syringe holder 5, the operator holds the distal portion of the syringe 2, 3 or 4 exposed from the syringe holder 5 and pulls out the same. For example, when connecting the syringe 2 from the balloon catheter 40, the plunger 7 is pulled back toward the proximal portion 2b side of the syringe 2 in advance.

When the syringe 2 is connected, the operator holds the flange 12a of the cylinder 6 and the pressing portion 21 of the plunger 7 between his/her fingers of one hand, and holds the cylinder 6 with the other hand and pushes the plunger 7 slowly toward the distal portion 6a of the cylinder 6.

No air is supplied to the balloon 42 (see FIG. 3) until the sealing surface 20a of the seal member 19a of the plunger 7 reaches the holes 14 and 15. In other words, no air is supplied to the balloon 42 because although the capacity defined by the seal member 19a and the interior of the cylinder 6 is reduced when the plunger 7 is pushed therein, air corresponding to the reduced capacity is released through the two holes 14 and 15 which have less resistance.

When the operator further pushes the plunger and hence the seal member 19a moves toward the distal portion 6a beyond the position where the holes 14 and 15 are formed, air starts to be supplied to the balloon 42. In other words, since the seal member 19a is positioned on the side of the distal portion 6a with respect to the holes 14 and 15, the air in the space in the cylinder 6 is not released any longer from the holes 14 and 15, and hence the air corresponding to the reduced capacity is sent to the balloon catheter 40 from the outlet port 9. The air is supplied to the balloon 42 through the expansion lumen 44 shown in FIG. 6. Consequently, the balloon 42 expands according to the reduced amount of the capacity in the cylinder 6 (see FIG. 7).

In other words, when the plunger 7 is pushed into the distal portion 6a, the amount of air corresponding to the first capacity is sent into the syringe 2, and hence the balloon 42 is expanded to an extent corresponding to the first capacity. When the syringe 3 is selected, the amount of air corresponding to the second capacity is sent thereto, so that the balloon 42 is expanded. When the syringe 4 is selected, the amount of air corresponding to the third capacity is sent thereto, and the balloon 42 is expanded.

When pushing the plunger 7, 23 or 27, the operator may place his/her fingers on the outer periphery of the cylinder 6, 22 or 26. In this case, he/she may clog one of the holes 14, 24, or 28 and the holes 15, 25 or 29 by his/her finger. However, in this embodiment, since the two holes are provided, there is no possibility that the two holes 14 and 15, 24 and 25, or 28 and 29 are clogged simultaneously, whereby the amount of air to be supplied to the balloon 42 can be reliably secured. In particular, since the two holes 14 and 15, 24 and 25, or 28 and 29 are formed at the positions shifted about 90° in the circumferential direction, even though one of these holes 14, 24 or 28 is clogged when the operator places the cylinder 6, 22 or 26 between his/her fingers, the other hole 15, 25 or 29 is kept unclogged.

In this embodiment, since the plurality of syringes 2, 3 and 4 are prepared according to the size of the balloon 42 to be expanded, and the syringes 2, 3 and 4 are stored in a line in the syringe holder 5, the syringes 2, 3 and 4 are prevented from scattered while they are stored in the sterilized package or when taking out from the sterilized package for use, and hence usability is improved. Also, since the syringes are not stored in the double sterilized packages as in the related art, the required syringe 2, 3, or 4 can be taken out quickly, and hence the time for manipulation can be reduced.

Since the distal portions of the syringes 2, 3 and 4 project from the syringe holder 5, the syringes 2, 3 and 4 can be taken out easily from the syringe holder 5.

The syringes 2, 3 and 4 may not have holes 14, 15, 24, 25, 28 and 29. Since the capacities in the cylinders 6, 22 and 26 of the syringes 2, 3 and 4 when the plungers 7, 23 and 27 are pulled back are different from each other, the balloon 42 can be expanded to different sizes respectively by the syringes 2, 3 and 4 even though the holes are not formed.

Subsequently, referring to the drawings, a second embodiment of the invention will be described. The same components as the first embodiment are represented by the same reference numerals. Description overlapped with the first embodiment will be omitted.

Figure 8:
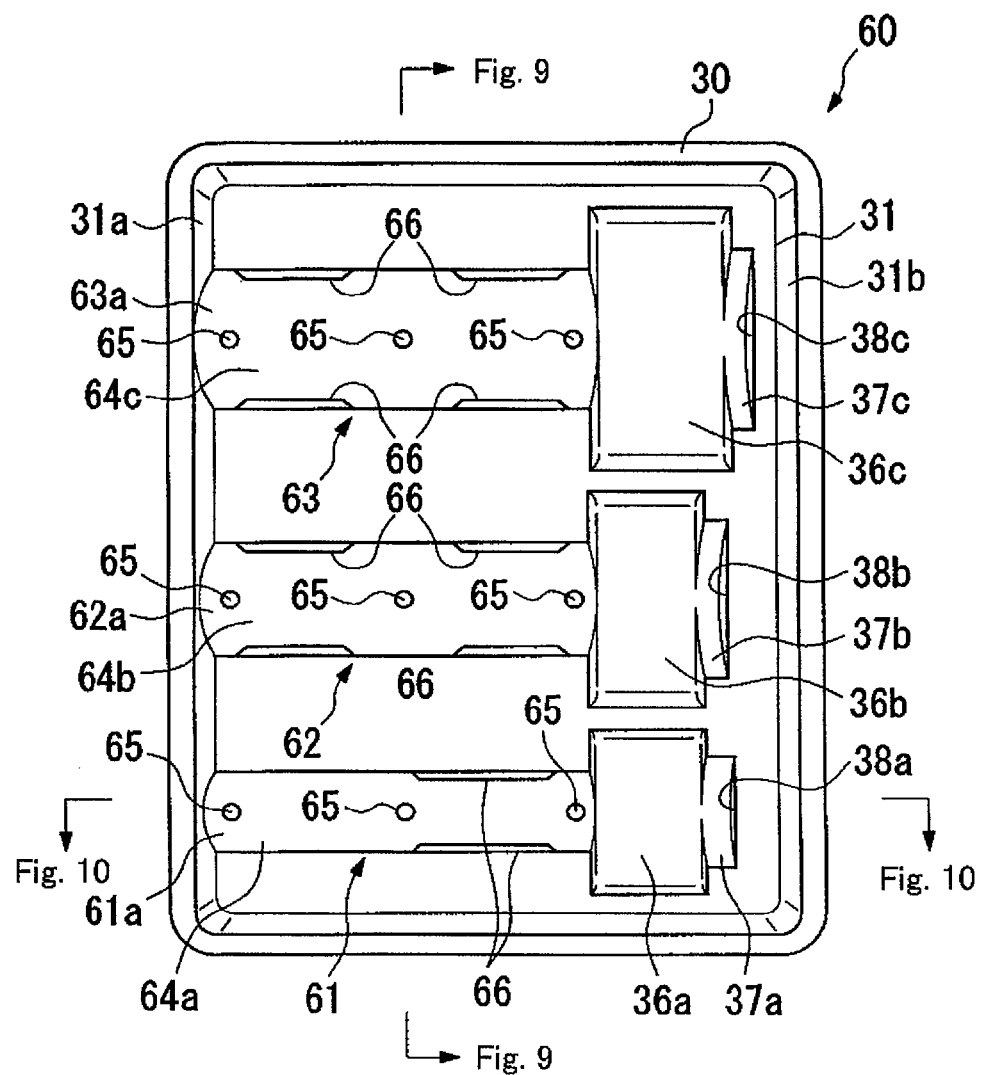
FIG. 8 is a top view of a syringe holder.

As shown in FIG. 8, a syringe holder 60 is provided with three recessed holding parts 61, 62 and 63 along the longer side thereof.

The respective holding parts 61, 62 and 63 extend from openings 61a, 62a and 63a which are formed on the side surface 31a of the main body 31 and then extended towards the side surface 31b. These holding parts 61, 62 and 63 differ from the first embodiment in the forms of cylinder storage grooves 64a, 64b and 64c.

Figure 9:
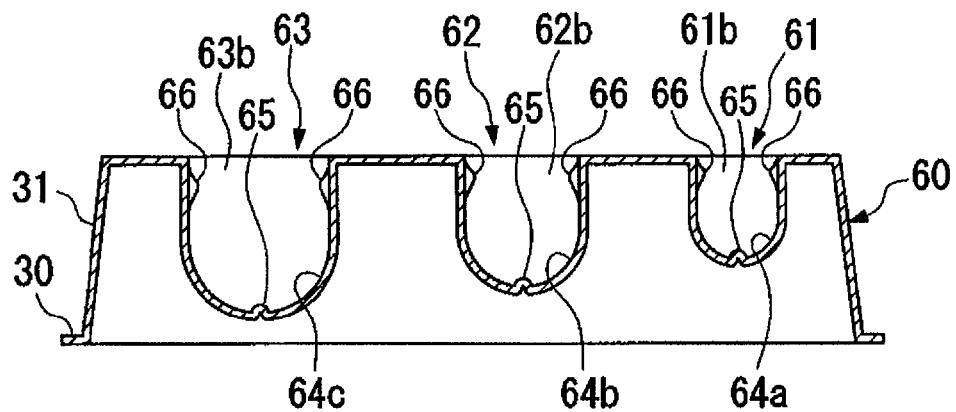
FIG. 9 is a cross-section of FIG. 8.

As shown in FIG. 8 and FIG. 9, the cylinder storage groove 64a is formed substantially into a U-shape, and the width and the depth thereof are formed to be larger than those of the cylinder 6 in diameter. A bottom portion of the cylinder storage groove 64a is formed with three protrusions 65 at regular intervals. The protrusions 65 have shape and size which come into point contact with the cylinder 6, and the height thereof is such that the upper surface of the cylinder 6 does not project from an upper opening 61b of the cylinder storage groove 64a in a state in which the cylinder 6 is placed on the protrusion 65.

Figure 10:
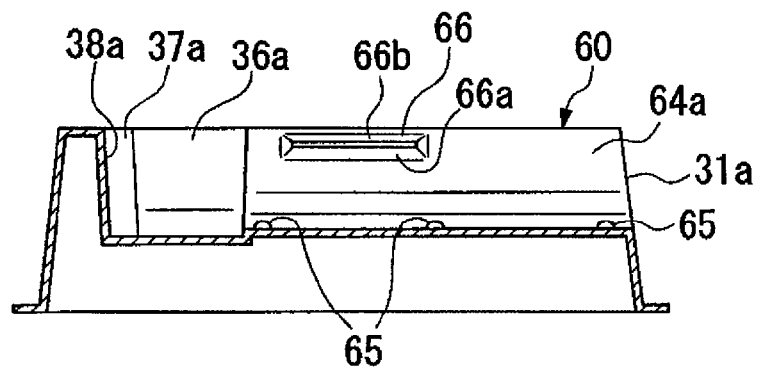
FIG. 10 is a cross-section of FIG. 8.

Furthermore, as shown in FIG. 9, the side walls near the upper opening 61b of the cylinder storage groove 64a are formed with protrusions 66 so as to protrude at opposed positions for reducing the width of the cylinder storage groove 64a. The positions where the protrusions 66 are formed are such that a predetermined clearance is formed with respect to the upper surface of the cylinder 6 in a state in which the cylinder 6 is placed on the protrusion 65. The protrusions 66 are reduced in width from the proximal portions continuing from the side walls of the cylinder storage groove 64a toward the distal portions, and the distal portions are formed into a flat surface extending in parallel with the vertical direction. As shown in FIG. 10, the inclination of a lower surface 66a of the protrusion 66, which is a side surface extending from the proximal portion to the distal portion, exposing itself to the bottom side of the cylinder storage groove 64a is less steep than an upper surface 66b. The protrusions 66 are disposed near the center of the main body 31 in the direction of the shorter side so as to oppose to each other, and extend in the direction of the length of the cylinder storage groove 64a respectively.

As shown in FIG. 8 and FIG. 9, the cylinder storage groove 64b of the holding part 62 is larger than the cylinder storage groove 64a in width and depth, and is formed with three protrusions 65 at the bottom thereof. The two each of protrusions 66 are formed near an upper opening 62b of the holding part 62 on the side walls of the cylinder storage groove 64b along the length of the cylinder storage groove 64b at opposed positions.

The cylinder storage groove 64c of the holding part 63 is larger than the cylinder storage groove 64b in width and depth, and three protrusions 65 are provided at the bottom thereof. The two each of protrusions 66 are formed near an upper opening 63b of the holding part 63 on the side walls of the cylinder storage groove 64c along the length of the cylinder storage groove 64c at opposed positions.

The operation of the syringe set will be described.

The syringe 2 is firstly stored in the holding part 61 of the syringe holder 60. When the syringe 2 is pushed into the holding part 61 from the upper opening 61b side so that the flange 12a of the cylinder 6 is stored in the flange storage groove 36a, the cylinder 6 is inserted therein so as to widen the distance between the protrusions 66, and is set in the cylinder storage groove 64a. After the cylinder 6 has passed, the protrusions 66 return to their original position.

In the stored state, the syringe 2 is supported mainly by the protrusions 65 at the bottom of the cylinder storage groove 64a. The cylinder storage groove 64a is larger than the syringe 2 so as to keep an allowance.

Likewise, the syringe 3 is stored in the holding part 62, and the syringe 4 is stored in the holding part 63. In this state, the respective syringes 3 and 4 are mainly supported by the protrusions 65 of the respective cylinder storage grooves 64b and 64c.

The syringe holder 60 in which the syringes 2, 3 and 4 are stored is placed in the sterilized package, and is subjected to sterilizing treatment together with the balloon catheter 40 and the like. At this time, since there are sufficient allowances between the syringes 2, 3 and 4 and the holding parts 61, 62 and 63, respectively, and the contact areas between the syringes 2, 3 and 4 and the holding parts 61, 62 and 63 are kept at the minimum areas owing to the protrusions 65, 66, gas can easily run through. Furthermore, since the flange storage grooves 36a, 36b and 36c and the plunger storage grooves 37a, 37b and 37c are formed into inclined surfaces or surfaces having the radius of curvature different from the syringes 2, 3 and 4 so as to form the clearances with respect to the syringes 2, 3 and 4, gas can easily run through. Therefore, the syringes 2, 3 and 4 are reliably sterilized by sterilizing gas.

In this embodiment, since the holding parts 61, 62 and 63 are formed so as to secure the sufficient allowances with respect to the syringes 2, 3 and 4, the clearances between the holding portions 61, 62, 63 and the syringes 2, 3, 4 are secured, whereby the syringes 2, 3 and 4 can be reliably sterilized. In particular, since the contact areas with respect to the syringes 2, 3 and 4 are reduced by means of the protrusions 65 and 66, sterilization of the syringes 2, 3 and 4 can be reliably performed.

Also, since the allowances are formed with respect to the syringes 2, 3 and 4, and the distal ends of the respective syringes 2, 3 and 4 are exposed, the syringes 2, 3 and 4 can easily be taken out.

Subsequently, referring to the drawings, a third embodiment of the invention will be described. The same components as the above-described embodiments are represented by the same reference numerals. Description overlapped with the above-described embodiments will be omitted.

This embodiment relates to a modification of the holding part.

Figure 11:
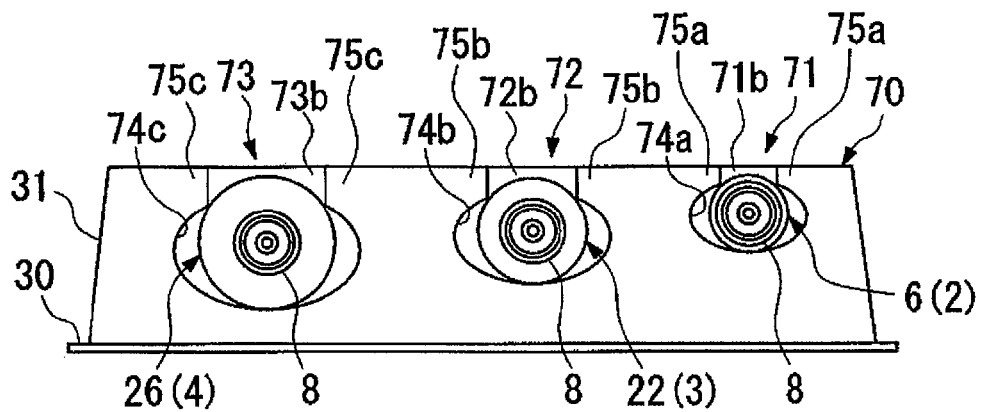
FIG. 11 is a drawing showing a cylinder storage groove.

As shown in FIG. 11, holding parts 71, 72 and 73 of a syringe holder 70 respectively have cylinder storage grooves 74a, 74b and 74c being substantially oval in cross-section.

The cylinder storage groove 74a is configured in such a manner that the portion near an upper opening 71b is protruded so as to be close to each other, so that protrusions 75a are formed, and the bottom side is formed into an oval shape. The number of contact portions between an inner wall of the cylinder storage groove 74a and the cylinder 6 are three positions at maximum including one on the bottom side and two on the side of the protrusions 75a. Each of them is subjected to linear contact. Other portions of the syringe 2 are not in contact with the holding part 71 and clearances are formed.

The cylinder storage groove 74b of the holding part 72 is larger than the cylinder storage groove 74a, is provided with protrusions 75b near an upper opening 72b, and is oval shape on the bottom side. The cylinder storage groove 74c of the holding part 73 is larger than the cylinder storage groove 74b, is provided with protrusions 75c near an upper opening 73b, and is oval shape on the bottom side.

Figure 12:
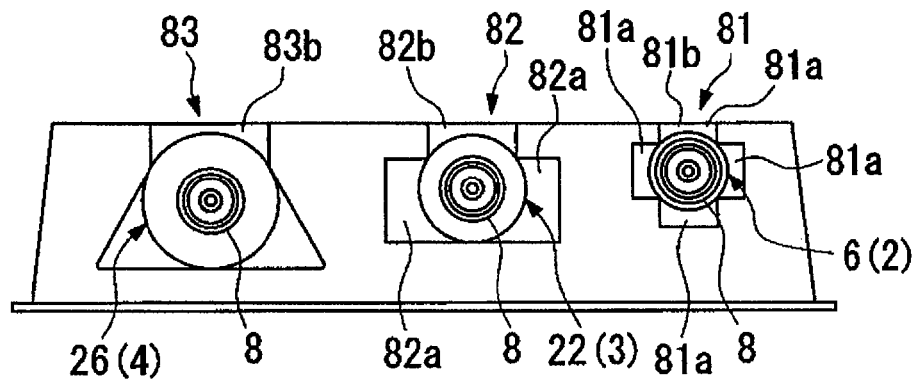
FIG. 12 is a drawing showing the cylinder storage groove.

They may be the cylinder storage grooves 81, 82 and 83 as shown in FIG. 12.

The cylinder storage groove 81 is substantially formed into a cross-shape with reference to an upper opening 81b. The cylinder 6 is mainly stored in a center portion of the cylinder storage groove 81, and clearances are defined with respect to the cylinder 6 by extended portions 81a extending in four directions from the center portion. The respective corners which correspond to the proximal ends of the extended portions 81a come into linear contact with the cylinder 6 at four positions at the maximum.

The cylinder storage groove 82 substantially formed into a T-shape with reference to an upper opening 82b. The width of the upper opening 82b is smaller than the cylinder 22. The bottom side is increased in width, and this widened portion 82a defines clearances with respect to the cylinder 22. The cylinder storage groove 82 is configured to come into linear contact with the cylinder 22 at three portions at the maximum including the corners of the widened portion 82a and the bottom.

The cylinder storage groove 83 is substantially formed into a triangular shape. In this case, the bottom corresponds to the bottom side of the triangle, and an upper opening 83b corresponds to one apex. The width of the upper opening 83b is smaller than the outer diameter of the cylinder 26, and the width of the portion near the bottom side is larger than the cylinder 26. The cylinder storage groove 83 is configured to define the clearance with respect to the cylinder 26, and contact with the cylinder 26 at three portions at the maximum including the bottom and the inclined two side walls.

This syringe holder may be composed of the three cylinder storage grooves of the same type selected from the cylinder storage grooves 81, 82 and 83.

With the cylinder storage grooves 74a, 74b, 74c, 81, 82 and 83, since the plurality of syringes 2, 3 and 4 can be held in line, usability is improved, and time for manipulation may be reduced. Since the clearances are defined between the syringes 2, 3 and 4 and the cylinder storage grooves 74a, 74b, 74c, 81, 82 and 83, gas can easily run through during gas sterilization, so that sufficient sterilization is achieved.

Referring to the drawings, a fourth embodiment of the invention will be described. The same components as the above-described embodiments are represented by the same reference numerals. Description overlapped with the above-described embodiments will be omitted.

Figure 13:
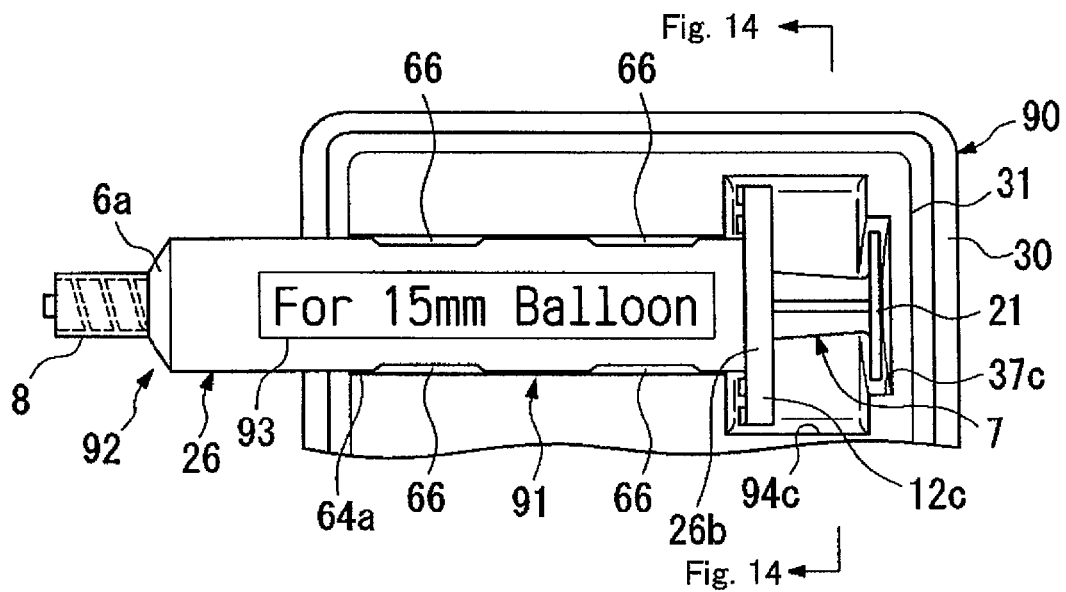
FIG. 13 is a top view of the syringe set.

FIG. 13 shows a state in which a syringe 92 is stored in a plurality of recessed holding parts 91 of a syringe holder 90.

The syringe 92 includes the cylinder 26, which is provided with an indication 93 on the outer peripheral surface at a position shifted from the direction of extension of the flange 12c by about 90° in the circumferential direction. In FIG. 13, the indication 93 includes a statement such as "For 15 mm balloon" or "15 mm". This indication means that this syringe 92 can expand the balloon 42 to a size corresponding to the expanded diameter of 15 mm at the maximum.

Figure 14:
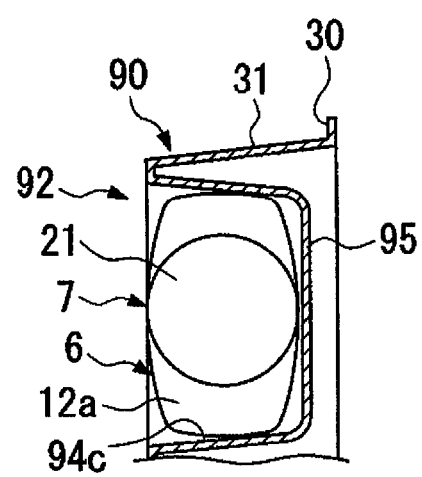
FIG. 14 is a cross-section of FIG. 13.

The holding part 91 of the syringe holder 90 differs from the holding part 61 in the second embodiment in the structure of a flange storage groove 94c. As shown in FIG. 14, the flange storage groove 94c includes a flat portion 95 as the bottom. The flat portion 95 is formed at a depth so that the flange 12c does not come into tight-contact with the flat portion 95 but the flat portion 95 prevents the rotation of the flange 12c when the syringe 92 is stored in the flange storage groove 94c. With this flat portion 95, movement in other directions, for example, the movement in the direction of extension of the flange 12c, or the movement in the direction of the depth of the flange storage groove 94c is allowed.

It is assumed that other holding parts, not shown, also have the flange storage grooves having the flat portions and are adapted to store other syringes so that the indications are visible.

Subsequently, the operation of the syringe holder 90 will be described.

The syringe 92 is inserted to the holding part 91 of the syringe holder 90 so that the indication 93 is faced upward. At this time, the orientation of the flange 12c of the syringe 92 is constrained by the flat portion 95 of the flange storage groove 94c, and the flange 12c is kept substantially in the horizontal direction. The indication 93 of the syringe 92 can always be viewed from above.

When the operator wants to expand the balloon 42 to a size corresponding to 15 mm in diameter, the operator checks the respective indications 93 and selects the syringe 92 with the corresponding indication. After having held the distal portion of the syringe 92 and taken it out from the syringe holder 90, the plunger 7 is pulled back to the proximal portion 26b and connected to the balloon catheter 40. When air is sent to the balloon 42 by the syringe 92, the balloon 42 is expanded to a size corresponding to 15 mm in diameter.

Although not shown in the drawing, other syringes, for example, when the syringe having the indication 93 showing that the balloon 42 can be expanded to 11.5 mm in diameter is used, the balloon 42 is expanded to a size corresponding to 11.5 mm in diameter. When the holes 14 and 15 are provided on the cylinder 26, a final diameter of the balloon 42 which can be expanded by the capacity from the distal portion 26a of the cylinder 26 to the position where the holes 14 and 15 are formed is shown in the indication 93.

In this embodiment, since the indication 93 is provided on the syringe 92 so that a rough standard of a size of the balloon 42 which can be expanded by the syringe 92 can be checked visually, selection of the syringe 92 can be performed smoothly, and the time for manipulation can be reduced.

Furthermore, since the flat portion 95 is provided in the flange storage groove 94c of the holding part 91 so that the rotation of the syringe 92 in the stored state is prevented, the indication 93 can always be placed on the upper surface of the syringe set. Therefore, the contents of the indication 93 can easily be confirmed.

The effects of facilitating handling, improving reliability of sterilization, and reducing time for manipulation by the structure of storing and holding the plurality of syringes 92 are the same as in the above-described embodiments.

The invention is not limited to the above-described embodiments, and may be widely applied.

For example, it is also possible to provide the protrusions 65 (see FIG. 8) in the cylinder storage grooves 71, 72 and 73 shown in FIG. 11 to further reduce the contact areas with respect to the cylinders.

It is also possible to provide the flat portion 95 (see FIG. 14) in the flange storage grooves 36a, 36b and 36c of the syringe holders 5 and 70 in the first embodiment and the third embodiment.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A syringe set including a plurality of syringes, individually selectable to be used to expand a balloon catheter to a corresponding size, the syringe set comprising;
    a first syringe configured to expand a balloon catheter to a first diameter including at least a first hole that communicates between an inside and an outside of the first syringe that are formed in a outer circumference of the first syringe, wherein a fluid capacity that is supplied from the first syringe by the first hole limits to a first capacity;
    a second syringe configured to expand the balloon catheter to a second diameter that is different from the first diameter, including at least a second hole that communicates between an inside and an outside of the second syringe that are formed in a outer circumference of the second syringe, wherein a fluid capacity that is supplied from the second syringe by the second hole limits to a second capacity that is different from the first capacity;
    a third syringe configured to expand a balloon catheter to a third diameter that is different from the first diameter and the second diameter, including at least a third hole that communicates between an inside and an outside of the third syringe that are formed in a outer circumference of the third syringe, wherein a fluid capacity that is supplied from the third syringe by the third hole limits to a third capacity that is different from the first capacity and the second capacity;
    a syringe holder that includes a plurality of holding parts each of which is uniquely structured to hold a corresponding syringe of a unique capacity size, the surgical holder including at least a first holding part, a second holding part, and a third holding part that are capable of fixing in part the outer circumference of the first syringe, the second syringe, and the third syringe respectively, to detachably hold the first syringe, the second syringe, wherein the first syringe, the second syringe, and the third syringe are arranged in the descending order among the first capacity, the second capacity, and the third capacity.

2. The syringe set for a balloon catheter according to claim 1, wherein the holding parts are formed to provide an allowance with respect to a surface contour of a corresponding syringe, a respective inner surface of each holding part including at least one protrusion.

3. The syringe set for a balloon catheter according to claim 1, wherein the holding parts are formed with a flat portion for constraining rotation of a syringe coming into abutment with a flange of the syringe.

4. The syringe set for a balloon catheter according to claim 1, wherein the holding parts are formed with an opening for allowing a distal portion on a side of a connecting portion, configured for connecting a syringe with the balloon catheter, to project therefrom.

5. The syringe set for a balloon catheter according to claim 1, wherein the holding parts include a storage groove, the storage groove including an opening for inserting a syringe.

6. The syringe set for a balloon catheter according to claim 5, wherein the storage groove includes a projection at an upper portion thereof for preventing a stored syringe from dropping off.

7. The syringe set for a balloon catheter according to claim 5, wherein the syringe holder is resilient, so when a syringe is inserted therein, the opening is widened by resilient deformation.

8. The syringe set for a balloon catheter according to claim 5, wherein the storage groove comprises at least a cylinder storage groove for storing a cylinder of the syringe, a flange storage groove for storing the flange of the syringe, and a plunger storage groove for storing a plunger of the syringe in communication with each other.

9. The syringe set for a balloon catheter according to claim 5, wherein the storage groove constrains rotation of the syringe in a circumferential direction.

10. The syringe set for a balloon catheter according to claim 1, wherein the syringe set includes a balloon catheter.

11. The syringe set for a balloon catheter according to claim 1, wherein the syringe set is enclosed in a single sterilized package.

12. The syringe set for a balloon catheter according to claim 11, wherein the holding parts have a non-circular cross-section which is substantially orthogonal to the direction of a length thereof.

13. The syringe set for a balloon catheter according to claim 1,
    the first syringe, the second syringe, and the third syringe have a different circumference shape respectively; and
    the first holding part, the second holding part, and the third holding part are formed into a shape according to the circumference shape of the first syringe, the second syringe, and the third syringe respectively, thereby holding the first syringe, the second syringe, and the third syringe in a different order is prevented.

14. The syringe set for a balloon catheter according to claim 13,
    the first syringe, the second syringe, and the third syringe are each formed with a scale; and
    the first hole, the second hole, and the third hole that limit an amount of air of the first syringe, the second syringe, and the third syringe respectively are formed so as to align with the scales.

15. The syringe set for a balloon catheter according to claim 14,
    the at least a first hole, the at least a second hole, and the at least a third hole each have two holes; and
    one hole is formed in a surface of the outer circumference and the other hole is formed in a position shifted from the one hole by a predetermined turn in a circumferential direction.

* * * * *